United States Patent [19]

Gimovsky

[11] 4,151,254
[45] Apr. 24, 1979

[54] ADSORPTION COLUMNS FOR USE IN RADIOIMMUNOASSAYS

[75] Inventor: Arlene J. Gimovsky, New York, N.Y.

[73] Assignee: Union Carbide Corporation, New York, N.Y.

[21] Appl. No.: 587,264

[22] Filed: Jun. 16, 1975

[51] Int. Cl.² ............................................. G01N 31/00
[52] U.S. Cl. ...................................... 422/71; 210/282; 210/289; 29/525
[58] Field of Search ............... 53/3; 23/230 R, 253 R, 23/230 B, 259; 210/282, 497 R, 198 C, 198 R, 259; 55/386; 29/525

[56] References Cited

U.S. PATENT DOCUMENTS

| 3,215,500 | 11/1965 | Bittner | 23/259 |
| 3,478,886 | 11/1969 | Hornbeck | 210/198 C |
| 3,630,683 | 12/1971 | Robb | 210/282 |
| 3,953,172 | 4/1976 | Shapiro et al. | 23/230 B |
| 3,973,313 | 8/1976 | Hunter | 29/525 X |

Primary Examiner—Ferris H. Lander
Attorney, Agent, or Firm—William Raymond Moran

[57] ABSTRACT

Adsorption columns are provided which can be utilized in radioimmunoassay systems, such as those involving the separation of antibody-antigen complexes from free antigens. The preparation of the columns includes the treatment of retaining substrate material to render it hydrophilic, preparation and degassing of the separation material and loading the column.

9 Claims, 1 Drawing Figure

U.S. Patent
Apr. 24, 1979
4,151,254
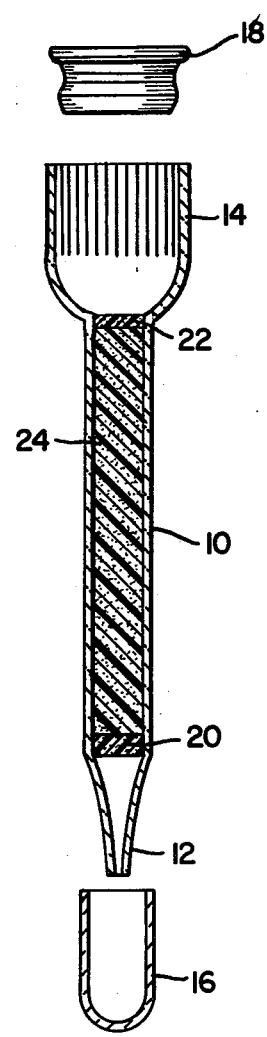

ADSORPTION COLUMNS FOR USE IN RADIOIMMUNOASSAYS

This invention relates in general to adsorption columns. In one aspect this invention relates to adsorption columns which are useful in radioimmunoassays. In a further aspect, this invention relates to a process for the preparation of columns.

Rapid, automatic analytical devices are currently in demand due to the ever increasing requirement for micro-analytical studies in biochemical research, routine clinical testing, enzymatic studies and the like. Multistation analytical devices which utilize a centrifugal field are presently becoming available for the rapid microanalysis of a wide variety of liquids such as body fluids, e.g., blood serum, food products, and the like.

In such devices it is often critical that a series of reactions be started at exactly the same time if reliable results are to be obtained. This is particularly important for enzymatic studies wherein measurements can often be taken after the reaction has proceeded for only a few seconds or minutes.

Certain of these devices can use adsorption columns to separate the components to be analyzed. However, when adsorption columns are utilized in devices which employ a centrifugal field, they have the added problem of column cracking or compaction due to loss of interstitial water. Since numerous analyses can be performed simultaneously, the columns must be inexpensive, uniform and easy to use.

Accordingly, one or more of the following objects will be achieved by the practice of this invention. It is an object of this invention to provide adsorption columns which are useful in radioimmunoassay systems. Another object of this invention is to provide adsorption columns which are utilized in an analytical system which employs centrifugal force for mixing and transferring reactants. A further object of this invention is to provide adsorption columns which can be safely stored until ready for use. Another object is to provide columns containing a uniform gel substrate. A still further object is to provide a process for the preparation of the columns. Another object is to provide a process rendering the retaining discs hydrophilic. A further object is to provide a process for loading and degassing the column.

These and other objects will readily become apparent to those skilled in the art in the light of the teachings herein set forth and the accompanying drawing.

The single drawing is a cross-sectional view of the adsorption column of this invention. The column 10 can be comprised of most any inert material such as glass, plastic and the like. A preferred material is polystyrene which is transparent light and not easily broken. Column 10 is approximately 4 inches long and has an outer barrel diameter of about 0.4 inches. It can contain approximately 2.5 milliliters of liquid. The tip 12 has an internal diameter of about 0.04 inches and the top reservoir 14 has an outer diameter of about 0.8 inches. Tip stopper 16 and stopper 18 seal the respective ends of the column. Retaining disc 20 and top disc 22 are comprised of a material, preferably plastic such as polyethylene, which has been rendered hydrophilic as hereinafter described. Gel 24 is contained within the barrel of the column between the two discs. Columns which can be employed are those supplied by the Sorstedt Company under the trade name, Sorpette.

In its broad aspect, the process of this invention is directed to adsorption columns useful in radioimmunoassays and to a process for this preparation. The columns are prepared by a process which comprises the steps of:

(1) inserting into a cylindrical column which is open at both ends and has a middle portion of essentially uniform diameter, a bottom portion which tapers to a lesser diameter than said middle portion, and an upper portion which is of a greater diameter than said middle portion, a first porous hydrophilic retaining member such that the first retaining member is disposed within said column at a point wherein the middle portion narrows to the lesser diameter, (2) filling the column with an aqueous slurry of a separation medium capable of selectively retaining one or more components which are submitted to the column, (3) inserting into the column a second porous hydrophilic retaining member so that the second retaining member is disposed within said column at a point on top of the separation medium approximately wherein the middle portion widens to the greater diameter, (4) admitting sufficient water to the top of the column to prevent the separation medium from drying, and (5) attaching removable sealing members to both ends of the column.

The preparation of the columns of this invention involve several factors which are important to obtain acceptable results. In the adsorption columns to be used in devices which employ a centrifugal field, it is important that the separation medium behaves as the limiting resistance to flow. Therefore, the top and bottom column retainers must pass liquid at a rate faster than that of the separation medium. However, the pore size of the bottom retainer must be smaller than the particle size of the medium retained. The separation particles should not be forced through the retainer material in the centrifugal field. Similarly, the pore size of the top retainer must be small enough to retain the separation medium during storage or transit wherein it could become inverted.

The material used as the column retainers must be able to withstand a centrifugal field of at least about five times gravity without cracking or bending. A variety of materials can be employed, although high density porous polyethylene is most highly preferred. Other materials which are less preferred are nylon, teflon copolymers of polyethylene, such as polyethylene-polypropylene copolymer, as the material chosen for the retainers must have an inherent flow into greater than that of the separation medium. It is for this reason that the use of the preferred polyethylene requires that it be converted to the hydrophilic state as hereinafter indicated.

The preferred material for use as retainers, as indicated, is high density porous polyethylene of about one-sixteenth inch in thickness and having a porosity of up to 30 microns and a durometer reading of from about 80 to about 100.

Example 1 of this disclosure describes the preparation of the retainers or discs. The treatment can be done prior to or after cutting the polyethylene sheet. While chromic acid is the preferred oxidant other oxidizing agents can also be employed. For example, nitric acid, perchloric acid, potassium permanganate, ozone, and the like can be employed. Thermal oxidation can also be employed if desired.

The particle size range of the separation medium is another important factor in order to ensure fast flowing adsorption columns. If an excess of fine particles relative to the means particle size is present in the columns, flow rates will decrease substantially. Conversely, columns containing an abundance of oversize particles relative to the mean particle size will lose interstitial water rapidly due to decreased cappillarity. This effect hastens cracking of the packed columns when not completely immersed in water, that is during spinning in the centrifugal field. Hence, the size range of particles used in the columns should be narrow enough to allow for uniform beds. A size range that is too broad can frequently result in an uneven distribution to each column and will harm separatory resolution.

In practice it has been observed that the adsorption media employed in the aforementioned centrifugal device should have a mean particle size within the range of from about 20 to about 80 microns. No more than 10 percent of the media particles should be outside of this range.

Although a variety of separation media can be employed this preferred column prepared by the process of this invention contain separations media composed of gels, gel combinations, ion exchange resins, and the like. Powdered or small beaded charcoal can also be employed but are presently less preferred. A particularly preferred media is a gel sold by Pharmacia under the tradename Sephadex-G-25 Fine and, wherein approximately 90 percent of the particles have a size of from about 20 to about 80 microns.

It has been observed that columns can be made from this gel as it is received. No elimination of fini particles is necessary as long as conditions are employed which blend this gel-water mixture without further subdividing the gel particles. In this respect it was noted after much experimentation that the use of a magnetic stirrer was undesirable since it tended to further subdivide the particles. The resulting gel solution was not uniform and when the columns were used in radioiminunoassays reproducible results were difficult to obtain. It was found that the use of an overhead stirrer was preferred and provided gel suspensions of uniform particle size.

A further feature which is important to the preparation of the columns of this invention is the separation medium to water ratio. The ratio is important to ensure uniform slurry volumes in each column thereby ensuring uniform separatory capability. In practice a ratio of the separation medium to water of from about 1:1.5 to 1.5:1 has been found to be satisfactory.

The gel prepared in accordance with the teachings of this invention should not be refrigerated since at low temperatures it is difficult to remove any air which may be entrapped.

As previously indicated the adsorption columns of this invention are particularly useful in radioimmunoassays, particularly those which employ centrifugal force for mixing, transferring and separating reactants and/or reaction products. The columns can, of course, be employed in other analytical procedures which do not utilize a centrifugal force, but offer no advantage over commercially available columns. Due to the fact that the gel suspension in the columns of this invention are subjected to centrifugal forces it is important that no cracking or compaction due to loss of interstitial water of the columns occur. Moreover, it is equally important that the rate of liquid flow through the gel suspension while under such a force be essentially uniform for all columns so that adsorption or desorption of the component(s) to be measured by uniform. All of these features are influenced by the process in which the columns are prepared.

A particularly preferred analytical device in which the adsorption columns of this invention can be employed is that disclosed in copending U.S. application Ser. No. 468,649 entitled "Method and Apparatus For Assaying Liquid Materials" filed May 10, 1974 now U.S. Pat. No. 3,953,172 and assigned to the same assignee as the instant invention. As disclosed therein, the device is a multistation analyzer which utilizes a centrifugal field for mixing, transferring and separating reactants and/or reaction products. The device can be controlled to allow partially mixing of components, time for incubation to occur and a simultaneous separation and measurement of components. For example, the adsorption column of this invention are conveniently utilized in this device for the radioimmunoassay of a variety of compositions such as body fluids, e.g., blood serum and the like. For example, adsorptions columns prepared in accordance with the procedures of examples 1-4 of this specification can be utilized for the microanalysis of digoxin, triiodothyronone (T-3), tetraiodothyronine (T-4), T-3 uptake, cortisol and the like.

The following examples are illustrative:

EXAMPLE 1

Column Disc Preparation

Polyethylene sheeting of approximately one sixteen inch in thickness and having a porosity of $25 \pm 3$ micron was cut into discs of 0.310–0.316 outside diameter. Thereafter the discs were immersed in acetone and swirled to remove any grease. While in the acetone bath, a vacuum was applied and immediately thereafter, the discs were immersed in water and rinsed using approximately one liter of water for every 500 discs. While in the water, a vacuum was applied again. The discs were transferred to a container partially filled with a strong oxidant to convert them from the hydrophobic to the hydrophilic state. The oxidant was a chromic acid solution prepared by dissolving 8-10 grams of potassium dichromate in 35-50 ml of distilled or deionized water in a 1500-2000 ml beaker followed by the gradual addition with stirring of one liter of concentrated sulfuric acid. The discs were allowed to remain in contact with the chromic acid until they turned green, usually about 5-10 minutes. Thereafter, the discs were removed from the acid and flushed with distilled water until they were white or cream colored. This washing step usually takes 5-10 minutes. The discs are sufficiently rinsed when the pH of the rinse water and the supply water are the same. The hydrophilic state of the discs is verified by placing a dry disc in an empty plastic column, seating it, and filling the column with water. The column should begin dripping immediately, indicating that the conversion from the hydrophobic to hydrophilic state is completed. The discs are stored under distilled or deionized water.

EXAMPLE 2

Preparation of Gel Suspension

A measured amount usually, from 40 to 50 grams, of a cross-linked dextran gel, sold under the trade name "Sephadex G-25 Fine" by Pharmacia Fine Chemicals Company, and having a bead size of 20–80 micron was transferred into a heavy wall Pyrex graduated beaker. Water, either distilled or deionized was added in an amount equal to 6–8 times the weight of gel. Thereafter, the mixture is stirred until the slurry is uniform. The mixture is then placed in a boiling water bath for a period of at least one hour. After allowing the slurry to cool the volume ratio of liquid level to the gel bed is adjusted so that the final ratio is approximately 1:0.8. Thereafter for everly 1000 ml volume of suspension is added 0.10 gram of a bacteriastatic agent such as Thimerosal.

EXAMPLE 3

Preparation of Gel Suspension

A measured amount usually from 40 to 50 grams, of the cross-linked dextran gel employed in Example 2 was transferred into a heavy wall Pyrex graduated beaker. Water, either distilled or deionized was added in an amount equal to 6–8 times the weight of gel thereafter, the mixture is stirred until the slurry is uniform. The mixture is then allowed to stand overnight at room temperature. The volume ratio of liquid level to gel bed was adjusted so that the final ratio is approximately 1:0.8. Thereafter for every 100 ml volume of suspension is added 0.10 gram of bacteriastatic agent Thimerosal. Prior to use, the slurry is degassed to remove all air bubbles.

EXAMPLE 4

Preparation of Column

Polystyrene columns having an outside diameter of the barrel of approximately 0.355 inches and a length of about 4.045 inches and supplied by the Walter Sarstedt Company, were placed upright in a rack contained in a tray. Each column was first rinsed with distilled or deionized water. Hydrophilic polyethylene discs prepared as in Example 1 were inserted into the lowest section of the main barrel of columns with a seating tool and wet with distilled water. The gel suspension, prepared in the manner set forth in Examples 2 or 3 was mixed by means of an overhead, variable speed stirrer at a moderate speed of 500 to 750 rpm to maintain a completely homogenous mixture. Thereafter 5.0 milliliters of the gel was dispensed into each of the pre-washed columns. The gel suspension was allowed to settle so that the resin bed level was approximately one-sixteenth of an inch above the main barrel of the column. At lease one to two milliliters of water are kept above the gel before the top disc is inserted. A second hydrophilic plug prepared as in Example 1 was placed in the upper section of the main barrel with a seating tool, the portion of each column above the disc was rinsed thoroughly with water to remove excess gel. Thereafter 3.0 to 4.0 milliliters of the gel swelling agent were added to each column and the reagent allowed to drip through the column until no liquid remained on the upper disc. The columns were then stored in distilled water which contained 0.01 volume percent of a bacteriostatic agent such as Thimerosol.

Although the invention has been illustrated by the preceding examples, it is not to be construed as being limited to the materials employed therein, but rather the invention relates to the generic area as hereinbefore described. Various modifications thereof can be made without departing from the spirit and scope thereof.

What is claimed is:

1. A process for the preparation of a disposable adsorption column useful for radioimmunoassays in a centrifugal field which process comprises the steps of:
    (1) inserting into a cylindrical column which is open at both ends and has a middle portion of essentially uniform diameter, a bottom protion which tapers to a lesser diameter than said middle portion, and an upper portion which is of a greater diameter than said middle portion, a first porous hydrophilic disc-shaped retaining member comprised of polyethylene and having a porosity of up to about 30 microns and capable of: (a) retaining a separation medium within said column, (b) withstanding a centrifugal filed of at least five times gravity without cracking or bending, and (c) passing liquid at a rate faster than that of said separation medium, said first retaining member having pores sized smaller than the size particles comprising said separation medium and being disposed within said column at a point wherein said middle portion narrows to said lesser diameter;
    (2) filling said middle portion of said column with an aqueous slurry of a separation medium comprised of a gel in water having a ratio of water to gel of from about 1:1.5 to about 1.5:1, said separation medium capable of selectively retaining one or more components which are admitted to said column, at least about 90 percent of the particles comprising said separation medium sized from about 20 to about 80 microns;
    (3) inserting into said column a second porous hydrophilic disc-shaped retaining member comprised of polyethylene and capable of: (a) retaining said separation medium within said column, (b) withstanding a centrifugal field of at least five times gravity without cracking or bending, and (c) passing liquid at a rate faster than that of said separation medium, said second retaining member having pores sized smaller than the size particles comprising said separation medium disposed within said column at a point on top of said separation medium approximately wherein said middle portion widens to said greater diameter;
    (4) admitting sufficient water to the top of said column to prevent said separation medium for drying, and
    (5) attaching removeable sealing means to both ends of said column.

2. The process of claim 1 wherein separation medium is comprised of a slurry of a gel which has an average mean particle size of from about 20 to about 80 microns.

3. The process of claim 1 wherein said separation medium is comprised of a slurry of cross-linked dextran in water.

4. The process of claim 1 wherein said separation medium is comprised of a slurry of charcoal in water.

5. The process of claim 2 wherein said members have a durometer reading from about 80 to about 100.

6. The process of claim 1 wherein said retaining members have been rendered hydrophilic by treatment with an oxidizing agent.

7. The process of claim 6 wherein said oxidizing agent is chromic acid.

8. The process of claim 6 wherein said retaining members prior to being contacted with said oxidizing agent are sequentially washed in acetone and water while under vacuum.

9. An adsorption column useful for radioimmunoassay prepared by the process of claim 1.

* * * * *